United States Patent [19]

Schutzer

[11] Patent Number: 5,187,065
[45] Date of Patent: Feb. 16, 1993

[54] METHOD AND MATERIALS FOR DETECTING LYME DISEASE

[76] Inventor: Steven E. Schutzer, 21 Canterbury Rd., Great Neck, N.Y. 11021

[21] Appl. No.: 455,175

[22] Filed: Dec. 22, 1989

[51] Int. Cl.$^5$ .................. G01N 33/569; G01N 33/564
[52] U.S. Cl. .................... 435/7.32; 435/7.92; 435/961; 436/507; 530/868; 530/412; 530/421
[58] Field of Search ............ 435/7.32, 7.92, 961, 435/968, 975; 436/518, 536, 539, 542, 800, 804, 808, 507; 530/868, 412, 413, 417, 421

[56] References Cited

U.S. PATENT DOCUMENTS 4,459,359  7/1984  Neurath ............................ 436/507
4,548,908  10/1985  Kameda ............................ 436/500

OTHER PUBLICATIONS

Dattwyler et al. "Seronegative Lyme Disease" New England Journal of Medicine 319(22) pp. 1441–1446 (Dec. 1, 1988).
Jones et al., "Isolation of Immune Complexes and Characterisation of their Constituent Antigens and Antibodies in some Human Diseases: A Review" J. Immunol. Methods 44 pp 219-270 (1981).
Allen C. Steere, "Pathogenesis of Lyme Disease, Implications for Rheumatic Disease," Annals New York Academy of Sciences, vol. 539 (1988), 87–92.
Hardin et al., "Immune Complexes & The Evolution of Lyme Arthritis," N. Eng. J. of Med., vol. 301, No. 25 (1979), 1358–1363.
Coyle et al., "Multiple Sclerosis Immune Complexes: An Analysis of Component Antigents & Antibodies," Annals of Neurology, vol. 16, No. 6 (1984), 660–667.
Volkman & Dattwyler, "Immunogiagnosis & Treatment of Lyme Borreliosis," Medical Times, vol. 11, No. 8 (1989), 59–71.
Trock & Craft, "Lyme Disease: A Clinical Perspective," Medical Times, vol. 117, No. 3 (1989), 56–65.
Alan G. Barbour, "The Diagnosis of Lyme Disease: Rewards & Perils," Annals of Internal Medicine, vol. 110, No. 7 (1989), 501–502.
Frederick W. Hyde et al., "Detection of Antigens in Urine of Mice & Humans Infected with *Borrelia burgdorferi*," J. Clinical Microbiology (1989), 58–61.
Allen C. Steere, "Medical Progress, Lyme Disease," N. Eng. J. of Med., vol. 321, No. 9 (1989), 586–596.
Burke A. Cunha, "The Many Manifestations of Lyme Disease," Emergency Medicine, (Feb. 15, 1989), 55–71.
"Bad News Regarding Early Detection of Lyme Disease," Internal Medicine News, vol. 23, No. 12, Jun. 15–30, 1989.
Clark, Jennifer, "Lyme Disease: Early Diagnosis is Imperative to Avoid Serious Late-Stage Complications," Modern Med., vol. 57, No. 6 (Jun., 1989).
Joseph E. Craft et al., "Antibody Response in Lyme Disease, Evaluation of Diagnostic Tests," J. Infec. Dis., vol. 149, No. 5, (May, 1984), 789–795.
Klaus Hoffken et al., "Dissocation & Isolation of Antigen & Antibody from Immune Complexes," J. Immun. Methods, vol. 53 (1982), 51–59.
Louis A. Magnarelli et al., "Enzyme–Linked Immunosorbent Assays for Lyme Disease," J. Infec. Dis., vol. 159, No. 1 (Jan., 1989), 43–48.
M. Digeon et al., "Detection of Circulating Immune Complexes in Human Sera Etc.," J. Immunological Methods, vol. 16 (1977), 165–183.

*Primary Examiner*—Esther L. Kepplinger
*Assistant Examiner*—Carol E. Bidwell
*Attorney, Agent, or Firm*—Klauber & Jackson

[57] ABSTRACT

A method for detecting the onset or presence of Lyme disease in a mammal, which comprises isolating a biological sample from the mammal, isolating from said biological sample any circulating immune complexes suspected to contain antibody reactive to *Borrelia burgdorferi*, dissociating the immune complexes so isolated, and examining the dissociated immune complexes for the presence of antibody. The present method offers a simple and reliable means for detecting Borrelia antibodies. Test kits and related methodology are also disclosed.

19 Claims, 1 Drawing Sheet

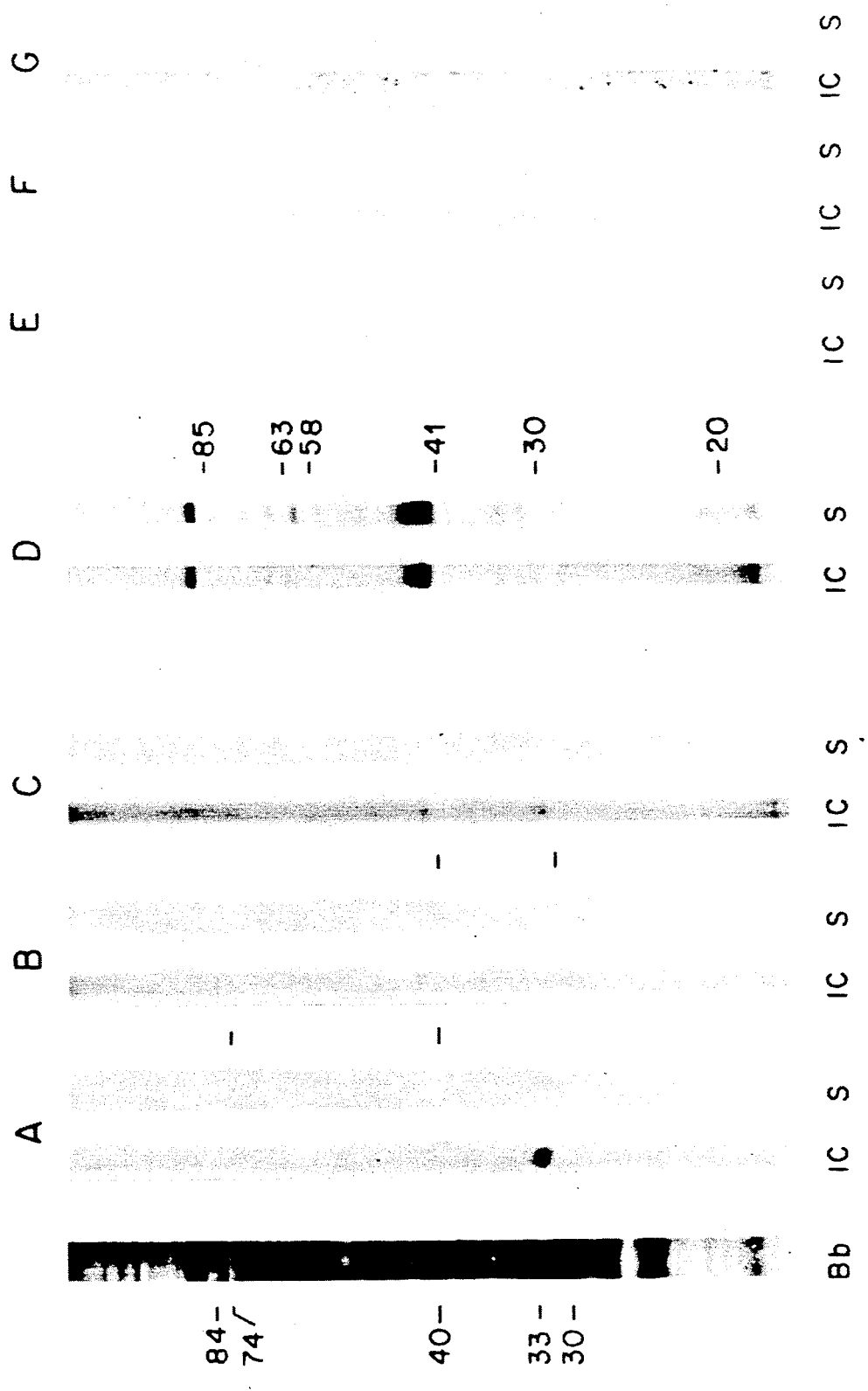

METHOD AND MATERIALS FOR DETECTING LYME DISEASE

RELATED PUBLICATIONS

The Applicant is author or co-author of articles, submitted or to be submitted for publication, directed to the subject matter of the present invention: (e.g. "Sequestration of Antibody to *Borrelia burgdorferi* in Immune Complexes in Seronegative Lyme Disease" (submitted for publication). The above listed articles are incorporated herein by reference.

BACKGROUND OF THE INVENTION

The present invention relates to the detection of Lyme disease, and particularly to the clinically reliable examination and detection of Lyme disease in instances of seronegativity in mammals and particularly in humans.

Seronegativity is one of the major obstacles to diagnosis of Lyme disease as well as a common unexplained feature of the disease. Lyme disease, etiologically linked to the spirochete, *Borrelia burgdorferi*, may present acutely or develop insidiously. Its manifestations are protean and may specifically involve the musculoskeletal, cardiovascular, cutaneous, and nervous systems. Some cases begin with a characteristic cutaneous lesion, erythema chronicum migrans (ECM), following a deer tick bite. However, many others are unaware of a tick bite or skin lesion, making diagnosis difficult, yet develop features of Lyme disease. Diagnosis is also complicated when symptomatic individuals are negative for *Borrelia burgdorferi* antibody despite sensitive serological assays. Untreated patients as well as patients who have received early antibiotic therapy may remain seronegative even when symptoms of infection persist.

In general, antibody may not be detected following exposure to an infectious agent either because it is bound or sequestered, and therefore hidden from conventional probes or because it is not secreted by B cells. Dattwyler et. al. have demonstrated that in Lyme disease, T cell reactivity towards *Borrelia burgdorferi* occurs even in the absence of significant specific antibody as detected by a sensitive ELISA (Dattwyler et al., N. ENGL. J. MED. (1988), 319:1441-1446).

Because of the inability to offer reliable detection of antibodies to *Borrelia burgdorferi*, and owing to the lack of predictability in the manifestation of visible symptoms of the disease such as ECM, a large population of those afflicted with the disease do not receive timely or adequate treatment and thereby risk far more serious consequences such as the development of a chronic condition and the more serious sequelae such as meningitis, chronic radiculoneuropathies, fatigue, cognitive problems, pericarditis, or arthritis. Likewise, the recent and dramatic increase in the incidence of Lyme disease and the corresponding lack of consistent and early diagnoses have severely compromised the ability to successfully treat this disease. A need therefore exists for a reliable procedure and associated materials which will facilitate the early and consistent diagnosis of the disease and permit the aggressive therapeutic protocols presently in existence as well as those under development, to be administered in timely fashion to arrest the progress of the disease and substantially reduce, if not eliminate, its continued progress and activity.

SUMMARY OF THE INVENTION

In accordance with the present invention, a method is disclosed for detecting the onset or presence of infection with *Borrelia burgdorferi*, the cause of Lyme disease in a mammal, which comprises:

A) isolating a biological sample from said mammal;

B) isolating from said biological sample any circulating immune complexes suspected to contain antibody reactive to *Borrelia burgdorferi* or the corresponding antigen;

C) dissociating said immune complexes isolated in step B); and

D) examining said dissociated immune complexes for the presence of said antibody and/or antigen.

The biological samples that may be isolated and examined for the presence of said immune complexes containing antibody to *Borrelia burgdorferi* may be retrieved from fluids such as synovial fluid, serum, cerebrospinal fluid (CSF) taken from the central nervous system of the mammal, or tissue. Each category of sample is useful in accordance with the present invention. Serum offers an accurate qualitative and perhaps quantitative assay when examined in accordance with the present procedures that will provide sufficient information for the commencement of aggressive antibiotic therapy at the initial stages of the onset of the disease, where certain of the neurological or arthritic manifestations are not yet in evidence, or at a later stage when the disease is suspected. The examination of samples from the CSF offers a more directed sophisticated qualitative analysis, as the locus and activity of the immune complexes in this sample may offer clues as to the particular neurological dysfunction or impairment that is either present or in development, so that adequate remedial therapeutic measures may be taken.

Once the immune complexes have been isolated, they are subjected to dissociation procedures to thereby isolate the various antibody and/or antigen components of such complexes and to resultingly facilitate the detection of any antibody to *Borrelia burgdorferi*. The procedures for isolation and dissociation of the immune complexes may be identified by use of a variety of assays; however, a particular assay involving polyethylene glycol (PEG) precipitation such as disclosed in Digeon et al., J. IMMUNOL. METHODS (1977); 16:165-183, is preferably utilized.

Likewise, the examination of the antibodies for the presence of reactive antibodies to *Borrelia burgdorferi* may be performed by one of several immunoassay procedures, including enzyme linked immunoassay (ELISA), although other assay procedures are likewise contemplated.

The present invention also relates to a method for determining the presence or onset of Lyme disease and/or any of the pathological states consequent or resultant therefrom in mammals, by measuring the reactivity and presence of antibodies to *Borrelia burgdorferi* isolated from immune complexes retrieved from fluids such as synovial fluid, serum, cerebrospinal fluid, or tissue. More particularly, the quantity or activity of the said antibodies to *Borrelia burgdorferi* may be followed directly by the assay techniques discussed later on, through the use of appropriately labeled antibodies or antigens.

Alternately, the antibodies to *Borrelia burgdorferi* can be used to raise binding partners or antibodies that could in turn, be labeled and introduced into a medium such as serum, to test for the presence of antibodies to *Borrelia burgdorferi* therein, and to thereby assess the state of the host from which the medium was drawn. In a further embodiment, the immune complexes might themselves be injected into a particular host to raise specific (eg. monoclonal) antibodies to a "neoantigenic" structure formed by an antibody to *Borrelia burgdorferi* combined to an antigen of *Borrelia burgdorferi*.

Thus, both the antibodies to *Borrelia burgdorferi* and any anti-idiotype or other antibodies that may be raised thereto, are capable of use in connection with various diagnostic techniques, including immunoassays, such as a radioimmunoassay, using for example, an antibody to the anti-*Borrelia burgdorferi* antibody that has been labeled by either radioactive addition, reduction with sodium borohydride, or radioiodination.

In an exemplary immunoassay, a control quantity of an antibody to *Borrelia burgdorferi*, its antibody, or the like may be prepared and labeled with an enzyme, a specific binding partner and/or a radioactive element, and may then be introduced into a synovial fluid, CSF, serum or tissue sample of a mammal suspected to have Lyme disease. After the labeled material or its binding partner(s) has had an opportunity to react with sites within the sample, the resulting mass may be examined by known techniques, which may vary with the nature of the label attached. A competitive assay may be performed between the known labeled antibody and the unknown quantity of a competitively reactive antibody from the sample.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, thermometric, amperometric, fluorospectro-photometric or gasometric techniques known in the art.

The materials developed and useful in accordance with the present invention includes an assay system which may be prepared in the form of a test kit for the quantitative analysis of the extent of the presence of the antibodies to *Borrelia burgdorferi*. The system or test kit may comprise sufficient quantity of a precipitation buffer solution for at least three separate preparations, and components of an immunoassay comprising a labeled component prepared by one of the radioactive and/or enzymatic techniques discussed herein, directly or indirectly coupling a label to the antibodies to *Borrelia burgdorferi:* and one or more additional immunochemical reagents, at least one of which is a free or immobilized ligand, capable either of binding with the labeled component, its binding partner, one of the components to be determined or their binding partner, and instructions for use of the kit. The preparation buffer may comprise a solution of PEG and sodium borate.

Accordingly, it is a first object of the present invention to provide a method for detecting the onset or presence of Lyme disease as a function of an infection with *Borrelia burgdorferi*.

It is a further object of the present invention to provide a method as aforesaid exists that may be performed in a facile and inexpensive manner.

It is a yet further object of the present invention to provide a dependable method for determining whether Lyme disease exists in a mammal with minimal, if any, false readings.

A still further object of the present invention is to provide a simple test kit for the performance of the present method.

A still further object of the present invention is to monitor the effectiveness of a drug regime or like protocol on a mammal known to have Lyme disease.

Other objects and advantages will become apparent to those skilled in the art from a review of the ensuing description which proceeds with reference to the following illustrative drawings.

BRIEF DESCRIPTION OF THE DRAWINGS

FIG. 1 is a depiction of comparative western blots of IgG antibodies to *Borrelia burgdorferi* in immune complex dissociated preparations and serum samples in seronegative Lyme disease patients.

Representative Western blots. *Borrelia burgdorferi* antigens were probed with the following specimens. Serum (S) from various patients (Pt) was used at a dilution of 1:100. Preparations of PEG-Na Borate dissociated immune complexes (IC) were run undiluted. Bb represents the control *Borrelia burgdorferi* (Bb) preparation stained by Auroprobe (Jansen). Patient A represents an ECM negative patient with antibody to *Borrelia burgdorferi* in the immune complex as determined by ELISA (BIC+). Patients B and C represent ECM positive/BIC+ patients. Patient D represents a known seropositive Lyme disease patient. Patients E, F, and G represent other disease controls. Not shown is conjugate run alone which was negative. Molecular weight (MW) markers in kilodaltons are indicated to the left and deduced MW indicated to the right of Pt D. A "—" is used to indicate specific bands.

DETAILED DESCRIPTION

The present invention relates to a method and associated materials for detecting Lyme disease infection in mammals. As used herein, the term "Lyme Disease" refers to the set of symptoms that results from the initial infection with *Borrelia burgdorferi*. This does not exclude symptoms that may result from cross reactive antibody that may be directed at target organs or tissue.

In accordance with the present invention, a method is disclosed for detecting the onset or presence of infection with *Borrelia burgdorferi*, the cause of Lyme disease in a mammal, which comprises:

A) isolating a biological sample from said mammal;

B) isolating from said biological sample any circulating immune complexes suspected to contain antigen or antibody reactive to *Borrelia burgdorferi;*

C) dissociating said immune complexes isolated in step B); and

D) examining said dissociated immune complexes for the presence of said antibody and/or said antigen.

The biological samples that may be isolated and examined for the presence of said immune complexes containing antibody to *Borrelia burgdorferi* may be retrieved from fluids such as synovial fluid, serum, cerebrospinal fluid (CSF) taken from the central nervous system of the mammal, or tissue, with serum and CSF preferred. Both serum and CSF are useful in accordance with the present invention, as the serum of the mammal offers an accurate qualitative and often quantitative assay when examined in accordance with the present procedures which will offer sufficient information for the commencement of aggressive antibiotic therapy at the initial stages of the onset of the disease, where certain of the neurological manifestations are not yet in evidence.

The examination of samples from the CSF, however, offers a more directed and sophisticated qualitative and quantitative analysis, as the locus and activity of the immune complexes in this sample may offer clues as to the particular neurological dysfunction or impairment that is either present or in development, so that adequate remedial therapeutic measures may be taken. Therapeutic response may also be followed by sequential analysis of the immune complex. Synovial fluid analysis may be similar to CSF analysis, as it likewise comes from a compartment.

The possibility that *Borrelia burgdorferi* specific antibody is synthesized but not detected because it is in complexed form was previously investigated but has been diagnostically discounted after Hardin et al., N.ENGL. J. MED. (1979) 301:25:1358. Hardin et al. showed that Clq binding to immune complexes occurred early but cleared with apparent recovery. Such binding persisted in those subjects with persistent disease (ie. neurologic or cardiac). In these cases the levels were significantly above normal and not just close to normal as has been found by the present inventor. Further, the authors found a disparity in Clq binding levels between synovial fluid and serum. Thus, reasoning from the results of Hardin et al., the assumption might be made that *Borrelia burgdorferi* antibody or antigen is present in immune complexes when Clq binding levels are high, and correspondingly, that it is not present in low level immune complexes in patients who have recovered from a demonstrative pathological state. It is this latter assumption that has been challenged by the discovery of the present invention.

More fundamentally, all of the present literature with regard to Lyme disease clearly acknowledges that there is at present no definitive and reliable test for detection of the anti-*Borrelia burgdorferi* antibody.

It is therefore surprising in this context that the present invention successfully predicates itself upon the isolation and dissociation of immune complexes to reliably retrieve anti-*Borrelia burgdorferi* antibody despite almost normal levels of immune complexes in seronegative patients.

Accordingly, the investigations that led to the present invention commenced by the isolation and examination of immune complexes (IC), simultaneously within a relatively restricted compartment, in the central nervous system (CNS) and peripheral blood. The presence of immune complexes in the cerebrospinal fluid (CSF) reflects an ongoing infectious, inflammatory, or autoimmune process, and the components of the immune complex are likely to contain antigen and antibody relevant to the pathogenetic process. Serum is also considered to be likely to contain relevant immune complexes, however, their analysis may be complicated by pathogenetically irrelevant components. Nevertheless, it was believed that the demonstration of *Borrelia burgdorferi* specific antibody and/or antigen in isolated complexes, might offer an explanation for some seronegative Lyme disease cases, and it might also lend insight into the pathogenetic mechanisms in Lyme disease.

Accordingly, the biological samples gathered in accordance with the present invention are then treated to isolate and thereafter dissociate the immune complexes that may reside therein. Specifically, the isolation of immune complexes and their characterization may be conducted in accordance with known procedures, utilizing equally well-known reagents, all as set forth in Jones et al., J. IMMUNOL. METHODS (1981), 44:249-270. The immune complexes may be isolated by polyethylene glycol precipitation, sucrose density gradient centrifugation and gel filtration, with polyethylene glycol precipitation being preferred herein. More particularly, polyethylene glycol of molecular weight 8000 may be utilized in conjunction with sodium borate, to concentrate the immune complexes.

Likewise, and as illustrated herein, isolation and dissociation of the immune complexes may be achieved using Raji cells, and subsequent analysis for specific antibodies may be achieved by use of a cell receptor assay also utilizing Raji cells. This procedure, however, is not preferred in view of the difficulties that are encountered in the culturing of sufficient Raji cells and the difficulty in discrimination with interfering antigen binding. However, synthetic or biologic analogs may be constructed with material that bears receptors for the immune complexes, which may be used as a substitute for the Raji cells.

Likewise, numerous reagents may be utilized and are known for the dissociation and elution of immune complexes, including both acid and alkaline buffers. For example, agents such as isotonic citrate at a pH of about 3.2 and EDTA at a pH of about 7.4 are purely exemplary. It is understood in the present instance that it is preferable to utilize sodium borate.

The present invention also relates to a variety of diagnostic applications, including methods for determining the presence of Lyme disease by reference to the ability to detect antibodies to *Borrelia burgdorferi* (also called herein "anti-Borrelia antibodies") by dissociation of resident immune complexes. As mentioned earlier, the antibodies to *Borrelia burgdorferi* and antigens of *Borrelia burgdorferi* can be used to produce antibodies by a variety of known techniques, and such anti-antibodies could then be isolated and utilized as in tests for Lyme disease in suspect mammals.

Antibody(ies) to the anti-*Borrelia burgdorferi* antibodies [ABA] can be produced and isolated by standard methods including the well known hybridoma techniques. For the purposes of the following general discussion, antibody(ies) to the anti-*Borrelia burgdorferi* antibodies be they from mammals or humans will be referred to generally herein as $Ab_1$, although antibody(ies) to the anti-*Borrelia burgdorferi* antibodies from mammals may from time to time be referred to herein as $Ab_m$ and antibody(ies) to the anti-*Borrelia burgdorferi* antibodies from humans may from time to time be referred to as $Ab_h$; and antibody(ies) raised in another species directed against the antibody(ies) from the mammal(s) to be tested will be designated $Ab_2$ or from time to time, $Ab_{os}$.

The presence of anti-*Borrelia burgdorferi* antibodies in the dissociated immune complexes in mammals can be ascertained by the usual immunological procedures applicable to such determinations. A number of useful procedures are known. Three such procedures which are especially useful utilize either the anti-*Borrelia burgdorferi* antibody labeled with a detectible label, antibody $Ab_1$ labeled with a detectible label, or antibody $Ab_2$ labeled with a detectable label. The procedures may be summarized by the following equations wherein the asterisk indicates that the particle is labeled, and [ABA] stands for the anti-*Borrelia burgdorferi* antibody.

A. $[ABA]^* + Ab_1 = [ABA]^* Ab_1$

B. [ABA]+Ab$_1$*=[ABA]Ab$_1$*
C. [ABA]+Ab$_1$+Ab$_2$*=[ABA]Ab$_1$Ab$_2$*
D. Carrier*[ABA]+Ab$_1$=Carrier*[ABA]Ab$_1$ These general procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. Re. 31,006 and 4,016,043. Still other procedures are known such as the "double antibody", or "DASP" procedure.

In each instance, the anti-*Borrelia burgdorferi* antibody forms complexes with one or more antibody(ies) or binding partners and one member of the complex (or a newly added member capable of detecting one of the already bound members) is labeled with a detectable label. The fact that a complex has formed and, if desired, the amount thereof, can be determined by known methods applicable to the detection of labels.

It will be seen from the above, that a characteristic property of Ab$_2$ is that it will react with Ab$_1$. This is because antibodies raised in one mammalian species have been used in another species as an antigen to raise antibodies such as Ab$_2$. For example, Ab$_2$ may be raised in goats using rabbit antibodies as antigens. Ab$_2$ therefore would be anti-rabbit antibody raised in goats. For purposes of this description and claims, [ABA] will be referred to as an anti-*Borrelia burgdorferi* antibody, Ag will be referred to as antigen to *Borrelia burgdorferi*, and Ab$_1$ will be referred to as a primary or anti[ABA]/anti-Ag antibody, and Ab$_2$ will be referred to as a secondary or anti-Ab$_1$ antibody.

Accordingly, an exemplary reaction may proceed as follows:

A. [ABA]+Ag=[ABA]Ag
B. [ABA]Ag+Ab$_{os}$*=[ABA]AgAb$_{os}$*

In the above reaction, [ABA] may come from a human subject and particularly from a patient's serum or CSF immune complex material after dissociation. Ag would be recovered from a sonicate of *Borrelia burgdorferi*, and may be fixed to a solid surface (ie. ELISA plate, western blot membrane, bead, biologic cell) or may be in solution. The new [ABA]Ag complex is detected by reaction with an antibody raised in goats against human Immunoglobulin (ie. one or all of IgG, IgA or IgM).

Naturally, the above procedures may be modified within the scope of the invention. Thus, the antigen Ag may be prepared from the corresponding synthetic peptide or active fragments thereof. Likewise, different enhancing reagents such as avidin-biotin may be used, and binding material other than an antibody may be used to immobilize the first antibody to be detected, eg. Staph A, Protein A, Cowan Strain, Conglutinin, etc.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The anti-*Borrelia burgdorferi* antibodies or their binding partner(s) can also be labeled with a radioactive element or with an enzyme. The radioactive label can be detected by any of the currently available counting procedures. The preferred isotope may be selected from $^{14}C$, $^{131}I$, $^3H$, $^{125}I$ and $^{35}S$.

Enzyme labels are likewise useful, and can be detected by any of the presently utilized colorimetric, spectrophotometric, fluorospectrophotometric, thermometric, amperometric or gasometric techniques. The enzyme is conjugated to the anti-anti-*Borrelia burgdorferi* antibodies, anti-*Borrelia burgdorferi* antibodies, antigens to *Borrelia burgdorferi*, or their binding partners or carrier molecules by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and alkaline phosphatase. U.S. Pat. Nos. 3,654,090; 3,850,752; and 4,016,043 are referred to by way of example for their disclosure of alternative labeling material and methods.

A particular assay system developed and utilized in accordance with the present invention to screen for drugs particularly responsive to the anti-*Borrelia burgdorferi* antibodies of a particular patient is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the anti-Borrelia antibodies recovered from a particular patient may be radiolabeled, after which binding studies would be carried out employing cells representative of the tissues characteristically affected by the Borrelia antigen or cross reactive antigen. Solutions would then be prepared that contain various quantities of labeled and unlabeled cell samples would then be inoculated and thereafter incubated. The resulting cell monolayers would then be washed, solubilized and then counted in a scintillation counter for a length of time sufficient to yield a standard error of <5%. These data are then subjected to Scatchard analysis after which observations and conclusions regarding material activity can be drawn. While the foregoing protocol is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of anti-*Borrelia burgdorferi* antibodies in a suspected mammal. For example, one class of such kits will contain at least a labeled component selected from the anti-*Borrelia burgdorferi* antibodies or their binding partners, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the detection of Lyme disease and the presence of the antigen *Borrelia burgdorferi*, comprising:

(a) a predetermined amount of at least one labeled immunochemically reactive component obtained by the direct or indirect attachment of anti-Borrelia antibodies or a specific binding partner thereto, to a detectable label;

(b) other reagents; and (c) directions for use of said kit.

More specifically, the diagnostic test kit may comprise:

(a) a known amount of at least one of the anti-*Borrelia burgdorferi* antibodies as described above (or a binding partner) generally bound to a solid phase to form an immunosorbent, or in the alternative, bound to a suitable tag, or plural such end products, etc. (or their binding partners) or at least one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling at least one of the anti-*Borrelia burgdorferi* antibodies to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the anti-*Borrelia burgdorferi* antibody and a specific binding partner thereto.

The following example is presented to illustrate the way in which the present method was developed and may be practiced.

EXAMPLE I

In this study, the immune complexes were examined in (1) the CSF of seropositive Lyme disease patients with prominent neurologic features and in (2) the serum from *Borrelia burgdorferi* seronegative symptomatic patients with either (a) a history of at least ECM or (b) without ECM but with symptoms consistent with Lyme disease. The neurologic CSF-Lyme disease group provided a model where the a priori detection of immune complexes indicates an abnormality. The seronegative groups represent a subgroup of a larger population in whom the diagnosis of Lyme disease proves to be the most difficult.

Material and Methods

Patients: Samples from two separate groups were studied.

Serum-Seronegative Group

The seronegative group was comprised of serum samples (n=22) which had been negative for *Borrelia burgdorferi* antibody in one or more assays such as the enzyme linked immunoabsorbent assay (ELISA) or a fluorescent ELISA (see Table 1). These samples were provided in a blinded manner and the clinical histories of these 22 were unknown to those performing the experiments until the completion of all the tests. These patients came from Monmouth and Ocean Counties, New Jersey, where outbreaks of Lyme disease have occurred. For the purposes of this study, definite Lyme disease (n=10) among these 22 symptomatic patients was defined by a history of ECM.

The other patients (n=12) of this seronegative group did not have a ECM-like rash but had inconclusive symptoms which suggested Lyme disease as part of a differential diagnosis. This subgroup was termed possible Lyme disease. Other disease controls included serum samples with similar levels of immune complexes; (n=9), seronegative patients from an endemic area with chronic fatigue (n=10), as well as those from seronegative asymptomatic individuals from the same endemic area. Known seropositive patients were used as positive controls.

TABLE 1

| Characteristics of Seronegative Patients of this Study | | |
|---|---|---|
| Parameter | ECM Positive (n = 10) | ECM Negative (n = 12) |
| Mean age in years | 35.4 ± 22.2 | 38 ± 9.2 |
| range) | (8–86) | (23–52) |
| Sex (M/F) | 3/7 | 7/5 |
| Time from onset of sample (months) | 25.8 ± 26.7 (1–81) | 22.4 ± 28.8 (4–78) |
| Clinical Manifestations | | |
| Minor CNS (headache, cognitive, mood) | 10 | 12 |
| Fatigue | 10 | 12 |
| Peripheral neuropathy | 7 | 7 |
| Arthralgias | 9 | 11 |
| Arthritis | 2 | 2 |
| Myalgias | 8 | 10 |
| Cardiac | 5 | 8 |
| Flu-like onset | 7 | 2 |
| Laboratory Positive Lyme (free Ab) tests | | |
| Fluorescent ELISA | 0 | 0 |
| ELISA* | 0 | 0 |
| Rheumatoid Factor* | 2 | 1 |
| Immune Complex Assays* (mean) | | |
| Anti C3 (+>15) | 3.3 µg Eq/ml | 2.4 µg Eq/ml |
| C1q binding (+>4) | 5.1 µg Eq/ml | 6.1 µg Eq/ml |

*Tests performed after entry into study

CSF-Neurologic Group

The CSF-neurologic group included CSF samples (n=31) from patients (n=30) with symptoms consistent with Lyme disease, particularly the neurologic manifestations (see Table 2). There were 17 males and 13 females ranging in age from 3 to 70 (mean 37) years. With the exception of one individual, who was positive on a T cell blastogenic assay with *Borrelia burgdorferi* all of these patients were seropositive for antibody to *Borrelia burgdorferi*. All patients came from an endemic area, Suffolk County, N.Y. Clinical manifestations included fatigue, headache, and cognitive impairment (12), radiculoneuropathy (6), headache ±neck pain (5), cranial neuropathy (4), intracranial hypertension (1), encephalopathy (1), and meningoencephalitis (1). Patient controls were derived from a panel of previously evaluated samples of back pain and other neurologic diseases.

TABLE 2

Characteristics of Seropositive Neurologic Lyme Disease Patients

| | Number of Patients | | | |
|---|---|---|---|---|
| Symptom complex | Total (n) | CSF Immune | Borrelia burgdorferi Specific Antibody in Immune Complex | Isotype in Immune Complex |
| Fatigue, headache, cognitive impairment | 12 | 7 | 1 | IgG |
| Radiculoneuropathy | 6 | 4 | 2 | IgG |
| Headache +/− neck pain | 5 | 2 | 0 | — |
| Cranial neuropathy | 4 | 4 | 2 | IgG, IgA |
| Acute encephalopathy | 1 | 1 | 1 | IgG, IgM |
| Intracranial hypertension | 1 | 1 | 1 | IgG |
| Meningoencephalitis | 1 | 1 | 1 | IgG, IgA, IgM |

Immunoglobulin studies ELISA for CSF and Serum Antibodies to *Borrelia burgdorferi*

Serum and CSF samples were tested for anti-*Borrelia burgdorferi* antibody in an ELISA. The ELISA was performed as previously described (Dattwyler et al., supra.) with minor modifications outlined below. The 96-flat bottom well microtiter plates were coated with a sonicate of *Borrelia burgdorferi* (5 μg per milliliter). CSF was diluted 1:1 and serum was diluted 1:500. A positive result was indicated by optical density readings greater than 3SD above the mean of a panel of healthy controls without a history of Borrelia infection. (Prior to entry into the study and prior to the above ELISA, a commercial fluorescent ELISA kit, Lyme FAST, 3M Santa Clara, Calif., was used according to kit instructions.)

Free Immunoglobulin Concentration in the CSF and Serum

An ELISA for human IgG, IgM and IgA was used to measure specific immunoglobulin content of the samples as previously reported.

Rheumatoid factor (RF) in Serum and CSF Samples

The presence of RF, which could potentially bind Borrelia reactive antibody, was screened in all samples by Latex agglutination (Rheuma-Fac, ICL Scientific, Fountain Valley, Calif.).

Electrophoresis and Western Blots

Western blots were performed to validate the composition of two well characterized preparations of antigens obtained from two different sources (3M, Santa Clara, Calif.; and Stony Brook) and to confirm the ELISA results of the immune complex dissociation experiments. These were performed as previously described with relevant modifications. Sonicates of cultured B31 strain *Borrelia burgdorferi* were used as the antigenic source (25 μg)/ 85 mm of membrane, and run on a preparative 10% sodium dodecyl sulfate-polyacrylamide gel with a 4% stacking gel electrophoresis (Mighty Small II system, Hoeffer, San Francisco). The separated proteins and molecular weight standards (Sigma) were transferred to nitrocellulose membranes which was developed in a 28 lane Miniblotter (Immunetics, Cambridge, Mass.) by previously reported methods. Specifically a 1:100 dilution of serum, or undiluted CSF, or 1:1 and 1:10 dilution of sodium borate-PEG immune complex preparation was added to each lane as the source of the first antibody. For the equivalence studies the appropriate dilution of serum or CSF was used, as well as several 10 fold concentration increases. Controls included known positive sera, conjugate alone, and known seronegative sera from patients with other diseases and matched for immune complex levels.

Immune Complex Detection Methods

More than one assay was used to assure the detection of a significant amount of immune complex material as they have different sizes and physicochemical properties.

Raji Cell Assay for Detection of Immune Complexes

To evaluate the levels of immune complexes in the CSF of neurologic Lyme disease we used the micro ELISA Raji cell system, based on C3 binding. The assay was also used to obtain quantitatively matched control specimens for the complexed Borrelia antibody studies below. The assay can detect as little as 1 μg/ml of AHG.

Polyethylene glycol (PEG)-ELISA

PEG precipitation, modified from the method of Digeon et al., Supra., was used both to detect and analyze immune complexes because it requires less manipulation of the material and has been successfully employed by us in the past to analyze fragile complexes in the CSF. Briefly, 0.9 ml of the sample was added to an equal volume of 7% PEG in 0.1M sodium borate pH 8.4, and incubated overnight at 4° C., then centrifuged at 8,320 g for 15 minutes. Pellets were washed twice using 3.5% PEG-borate and resuspended in 0.9 cc of 0.1M sodium borate, pH 10.2. The precipitate was probed for IgG, IgA, and IgM and the optical densities read on the micro ELISA reader as previously reported. Normal values were derived from PEG precipitations of normal control samples. The presence of immune complexes was considered significant when the immunoglobulin values in the PEG precipitates were greater than 3 standard deviations above the mean of the normal controls.

Anti-C3 Immune Complex Assay

The assay was performed in a similar manner to the above ELISAs according to kit instructions (Raji Cell Replacement EIA, Cytotech, San Diego, Calif.). A murine monoclonal fixed to microtiter wells, with specificity to iC3b, C3d,g and C3d activation fragments of C3, was used to bind circulating immune complexes containing these in 100 μl duplicates of serum samples diluted 1:50. Heat AHG standardized controls were used to generate a standard curve so that sample values could be expressed as µg Eq/ml. HRP-conjugated mouse anti-human IgG was used to detect the bound immune complex. Results were confirmed by preparing 1:50 duplicate sample dilutions, in the sample diluent to which anti C3 fragment antibody had been added. A reduction of the µg Eq/ml by >50% confirmed the results.

CIg Immune Complex Detection

The assay was performed in an identical manner to the anti C3 assay except for the following modifications. Purified human C1q fixed to microtiter wells (CIC EIA, Cytotech, San Diego, Calif.), was used to bind circulating immune complexes with affinity for C1q. HRP-conjugated goat anti-human IgG was used as the second antibody. Positive results were confirmed with the use of a diluent with a high salt concentration, 1.2M NaCl, which inhibits binding of circulating immune complexes. A reduction of the µg Eq/ml by >30% confirmed the results with the caveat that specimens with anti C1q antibody may not have this reduction.

Immune Complex Dissociation and Analysis of Components Raji Cell Elution

Immune complexes were isolated by binding and eluting from the Raji cell surface as previously described. In brief, serum or CSF was incubated with Raji cells ($3 \times 10^7$ cells per 0.4 ml) for one hour at 37° C. Cells were then washed 3 times with PBS; bound, complexes were eluted by adding 0.1M sodium borate, pH 10.2 (0.4 ml per $3 \times 10^6$ cells) for 20 min. Cells were sedimented by centrifugation, and the cell-free eluate (containing dissociated antigen and antibody) was collected for further analysis. Controls run in tandem included PBS, or human sera negative for immune complexes, as well as immune complex positive serum from patients with other diseases.

Polyethylene glycol (PEG)-ELISA

PEG precipitated immune complexes were brought up in sodium borate and then analyzed for *Borrelia burgdorferi* antibody and antigen.

Anti-Borrelia burgdorferi Antibody in Isolated CSF and Serum Immune Complexes The above ELISA assay for detection of anti *Borrelia burgdorferi* antibody was used to probe the dissociated CSF and serum immune complexes preparations.

Borrelia burgdorferi Specific CSF and Serum Antibody Activity in Immune Complex versus Free Immunoglobulin.

The above ELISA systems were used after appropriate dilutions of the CSF and serum were made such that the free and bound concentrations of IgG, then IgA, then IgM were equal. The results were expressed in ratio's of optical density readings (data not shown). With Western blots, the intensity of the bands were noted as well as the appearance of new bands.

Probe for Borrelia burgdorferi Antigen in CSF and Serum Immune Complexes

The SDS-PAGE and Western blot, described above, were used to analyze the dissociated CSF PEG immune complex preparations. Undiluted, 1:10, and 1:50 dilutions of these were loaded simultaneously with the known *Borrelia burgdorferi* preparations which had been serially diluted to ascertain thresholds of detection. Affinity purified human IgG with a very high anti-*Borrelia burgdorferi* antibody titer was used to probe for antigen.

Statistical Analysis

Fisher's exact test was applied to results obtained from the study of *Borrelia burgdorferi* reactive antibody in the isolated serum immune complex in 22 seronegative patients suspected of Lyme disease.

RESULTS

Serum-Seronegative Group

Borrelia burgdorferi Specific Free Serum Antibody in Putative Seronegative Lyme Disease Patients All of the 22 putative (i.e., previously negative on one or more assays) seronegative serum samples were non reactive for anti-*Borrelia burgdorferi* antibody in the ELISA using a previously established conservative threshold of 3 SD (see Table 1). In fact, 21 of 22 were <1 SD and 1 of 22 was between 1 and 2 SD.

Circulating Immune Complexes Levels in Serum

Among the seronegative Lyme disease patients with ECM we found that 5 of 10 patients had a positive value in the C1q assay above 4 µg Eq/ml compared to 9 of 12 ECM negative patients. The mean levels were 5.1 and 6.1 µg Eq/ml respectively. The anti-C3 immune complex assays values were not above a positive threshold of 15 µg Eq/ml in either group. The mean values were 3.3 and 2.4 µg Eq/ml for the ECM positive and negative groups. See Table 1. There was no significant association between these groups and a particular level of immune complexes. Relatively low levels without statistical significance between groups was also noted with respect to the presence or absence of an anti *Borrelia burgdorferi* antibody containing immune complex. These results did provide for matched levels when assaying for the *Borrelia burgdorferi* specific immune complexes.

Anti-Borrelia burgdorferi Antibody in Isolated Serum Immune Complexes

Immune complexes isolated from PEG precipitated sera samples of 22 seronegative patients who had either a definite diagnosis of Lyme disease, based upon the documentation of ECM, or only a possible diagnosis of Lyme disease with symptoms compatible with Lyme disease but without the ECM, were analyzed with respect to the presence of complexed *Borrelia burgdorferi* antibody. After completion of the experiments it was revealed that there were a total of 10 patients who were clinically diagnosed to have definite Lyme disease and 12 with a possibility of the disease (see Table 1).

In the ELISA analysis, anti-*Borrelia burgdorferi* IgG and IgM were probed. As shown in Table 3, among the definitive, ECM positive, Lyme disease cases, 10 of 10 (100%) patients had *Borrelia burgdorferi* specific antibody that had been sequestered in the immune complex. Included in this group is one patient who had not had antibiotic therapy before the sample was obtained. Among the 12 patients with a possible diagnosis of Lyme disease, 4 of 12 (33%) had anti-*Borrelia burgdorferi* antibody containing immune complexes (IgG). There was a significant association (Fisher's exact test, 1 degree of freedom, $p = 5.0 \times 10^{-8}$ a between the isolation of immune complexes containing anti-*Borrelia burgdorferi* antibody and ECM positive Lyme disease cases. See Table 3. Nine of the above 10 (90%) ECM/IC positive samples were of the IgG isotype and 2 of these 10 (20%) were of the IgM isotype (see Table 4).

Western blot confirmed the appearance of *Borrelia burgdorferi* reactive antibody which had been sequestered from detection prior to PEG-borate dissociation of the immune complex. In the representative blots shown in FIG. 1, it appears that IgG antibody is liberated from the complex to react against 41 kD in most cases, and also a 30 kD band in some samples. At the equivalent dilution of serum, a 41 kD band was clearly visible in the seropositive controls but absent or barely discernable in the seronegative Lyme disease patients and other controls.

Rheumatoid factor (RF) in Serum Samples

Rheumatoid factor (RF) screened among the 22 serum samples showed a positive reaction in one patient with definite Lyme disease and IgG anti-*Borrelia burgdorferi* positive immune complexes; a positive reaction in a possible Lyme disease patient without anti *Borrelia burgdorferi* positive immune complexes. A slightly positive reaction was found in a patient with definite Lyme disease and IgG anti-*Borrelia burgdorferi* positive immune complexes. The remaining 19 were negative in this test (see Table 4).

CSF-Neurologic Group (See Table 2)

CSF Free Immunoglobulin levels and Immune Complexes in Neurologic Lyme Disease Patients As measured by ELISA, free CSF IgG, IgA, and IgM were elevated in three patients with acute syndromes. Single patients had elevations in IgG and IgM, IgG and IgA, IgG, IgA, and IgM.

Using as a cutoff greater than 3SD above controls, the combination of PEG and Raji cell assays detected the presence of CSF immune complexes in 21 of 31 samples (68%). 19 of 31 (61%) samples were detected by PEG, 6 of 28 (29%) were detected by Raji, 6 of these (75%) were detected by both assays, and 2 of 28 (7%) samples by only Raji. All samples were negative for rheumatoid factor.

Immunoglobulin Isotype of CSF Immune Complexes (IC)

Using a 3SD cutoff, PEG precipitation showed IgG IC in 16 of 31 samples (52%), IgA IC in 6 of 31 samples (19%), and IgM IC in 9 of 31 samples (29%). The Raji cell assay showed IgG IC in 8 of 28 samples (29%).

*Borrelia burgdorferi* Specific CSF Immune Complexes

PEG isolated immune complexes contained anti-*Borrelia burgdorferi* IgG in 7 of 18 samples (39%), anti-*Borrelia burgdorferi* IgA in 2 of 6 samples (33%), and anti-*Borrelia burgdorferi* IgM in 3 of 7 samples (43%). See Table 5. *Borrelia burgdorferi* antigen (level of detection >100 ng) was not detected in any of the isolated immune complexes.

A second type of assay was also employed to isolate and dissociate immune complexes and then probe for specific IgG antibody. The Raji cell elution technique detected IgG *Borrelia burgdorferi* reactive antibody in 2 of 7 (29%) samples.

Combined use of both assays enabled detection of 8 of 19 immune complex samples with IgG *Borrelia burgdorferi* reactive antibody.

TABLE 3

Anti *Borrelia burgdorferi* Antibody Positive and Negative Immune Complexes in Seronegative Patients

| Group | Immune Complexes with Antibody to *B. burgdorferi* | Immune Complexes without Antibody to *B. burgdorferi* | Significance (compared to other diseases) P value |
|---|---|---|---|
| ECM + (n = 10) | 10 | 0 | $5.0 \times 10^{-8}$ |
| ECM − (n = 12) | 4 | 8 | $1.6 \times 10^{-2}$ |
| Controls: | | | |
| Seropositive Lyme disease (n = 22) | 21 | 1 | $<10^{-8}$ |
| Other diseases (n = 19) | 0 | 19 | — |

Note:
(9 IC level matched patients with asthma, urticaria, upper respiratory infection, polyradiculoneuropathy, allergy, multiple sclerosis, polymitosis, stroke; 10 chronic fatigue patients from endemic Lyme disease area)

TABLE 4

Immune Complexes (IC) Levels and Ig Isotypes Among Seronegative Patients with Anti-*Borrelia burgdorferi* Antibody Positive and Negative IC

| Parameter | Immune Complexes with Antibody to *Borrelia burgdorferi* | Immune Complexes without Antibody to *Borrelia burgdorferi* |
|---|---|---|
| Isotype in *Borrelia burgdorferi* Ab + IC | | |
| IgG | 9 (90%) | — |
| IgM | 2 (20%) | — |
| Rheumatoid Factor | 2 | 1 |
| IC Assay (mean) | | |
| Anti C3 | 3.4 µg Eq/ml | 2.3 µg Eq/ml |
| C1q | 5.2 µg Eq/ml | 6.0 µg Eq/ml |

Free versus Complexed Anti-*Borrelia burgdorferi* Antibody in CSF

Among 30 patients, 9 (30%) had at least one anti-*Borrelia burgdorferi* immunoglobulin isotype containing immune complexes. As seen in Table 5, comparisons of the relative specific reactivity within each isotype class of Ig between the bound and free Ig fractions revealed that of 6 CSF samples with *Borrelia burgdorferi* specific IgG IC, 2 had predominantly complexed anti-*Borrelia burgdorferi* antibody and 3 predominantly free antibody.

All 3 patients with *Borrelia burgdorferi* specific IgM IC antibody showed predominantly complexed antibody. Of 2 samples with *Borrelia burgdorferi* specific IgA IC, 1 had predominantly complexed antibody. Patients with predominantly complexed anti-*Borrelia burgdorferi* antibody had acute fulminant syndromes.

occurring in the serum and CSF of Lyme disease patients.

This is indirectly supported by the recent findings of Dattwyler et al. which demonstrate that *Borrelia burgdorferi* does not escape recognition of the immune system despite the apparent absence of a significant anti-

TABLE 5

Isotype of Immunoglobulin in CSF Immune Complexes of Neurologic Lyme Disease Patients

| | Number of Patients with | | |
|---|---|---|---|
| Isotype | Immune Complexes with Antibody to *Borrelia burgdorferi* | Immune Complexes without Antibody to *Borrelia burgdorferi* | Predominance of Bound versus Free Antibody to *Borrelia burgdorferi* |
| IgG | 7 | 11 | 2 of 6 |
| IgA | 2 | 4 | 1 of 2 |
| IgM | 3 | 4 | 3 of 3 |

As an independent verification, two untreated CSF specimens representing the positive IgG anti-*Borrelia burgdorferi* PEG-IC samples were analyzed, in a reference lab (3M), using the same antigen preparation as in one of our ELISA experiments. Included were untreated CSF samples from 3 multiple sclerosis patients who had been positive for PEG-IgG IC. All 5 were non reactive for *Borrelia burgdorferi* antibody in a 1:1 dilution confirming the apparent liberation of reactive *Borrelia burgdorferi* antibody after immune complex dissociation (see Table 6).

TABLE 6

Comparison of Neurologic Groups Immune Complexes After Antibody Tests in a Reference Laboratory

| | | *Borrelia burgdorferi* Specific Antibody in Isolated CSF Immune Complexes | |
|---|---|---|---|
| Category | Number of Patients | Present | Absent |
| Neurologic Lyme Disease with Free *Borrelia burgdorferi* CSF Antibody | 2 | 2 | 0 |
| Neurologic Lyme Disease without Free *Borrelia burgdorferi* CSF Antibody | 2 | 2 | 0 |
| Multiple sclerosis with immune complexes but without Free *Borrelia burgdorferi* CSF Antibody | 3 | 0 | 3 |

Detection of Complexed *B. burgdorferi* Antigen in Serum Immune Complexes

In 5 out of 5 patients with complexed anti-*B. burgdorferi* antibody, antigens which co-migrated with known *B. burgdorferi* antigens could be demonstrated.

DISCUSSION

Lyme disease is difficult to diagnose in symptomatic patients when the early presenting sign, the characteristic ECM rash, is not observed or when the serologic test is negative. Seronegative tests are found in many patients believed to have Lyme disease including those who have had ECM. This discrepancy prompted us to investigate the possibility that antibody to *Borrelia burgdorferi* is produced in these apparent seronegative patients but is not detected by conventional probes because it is sequestered in the form of circulating immune complexes. Our data clearly demonstrate that this is body response as can be detected by a sensitive ELISA. They demonstrated T cell recognition of *Borrelia burgdorferi* in a lymphocyte stimulation assay. Further support of the concept of sequestration of antibody and the use of immune complex dissociation techniques can be found in the study of other diseases. It has been demonstrated in several diseases including syphilis, that specific antibody may be produced and found in complexed form. Consequently, antibody may be sequestered from detection because it is bound to antigen in the form of a circulating immune complex or is bound to tissue antigen. Regardless of the actual circulating level, the complexed antibody may be detected when techniques are used to isolate the complex and dissociate the antibody from its target antigen.

Specifically, our studies demonstrate that in the peripheral blood system synthesized anti-*Borrelia burgdorferi* antibody appears to be bound in circulating immune complexes in the majority of the seronegative ECM positive patients when evaluated by ELISA. Western blots which confirmed the ELISA results also demonstrated the liberation of complexed antibody reactive to several antigens of *Borrelia burgdorferi*. These seronegative Lyme disease patients as well as other infected individuals may also have anti-*Borrelia burgdorferi* antibody which is tissue bound and is thus sequestered from detection. This of course does not rule out other possibilities as mechanistically important in other individuals or even the same individual at different times in the course of the disease.

Further support for this as a mechanism of seronegativity as well as a significant feature even in seropositive Lyme disease patients is the finding of complexed anti-*Borrelia burgdorferi* antibody in 3 seronegative patients with positive T cell mediated immunity (CMI) to Borrelia and 3 longitudinally followed patients who eventually seroconverted. Initially only complexed anti-*Borrelia burgdorferi* antibody was found in 3 of 3 seronegative patients, 2 of whom later converted to seropositive and the third to borderline positive. One ECM positive patient had complexed anti-*Borrelia burgdorferi* IgM at 2 weeks, began therapy, and 2 weeks later had a decrease of complexed, but rise of free, anti-*Borrelia burgdorferi* IgM. In contrast to this more rapid transition, one patient undiagnosed and not treated with antibodies for one year had complexed IgG anti-*Borrelia burgdorferi* antibody in two samples a year apart, and seroconverted after therapy in 8 months.

Among patients with seropositive or T-lymphoblastogenic mitogen positive neurologic Lyme disease, we had previously shown that the presence of CSF immune complexes was the most outstanding abnormal CSF parameter when compared to pleocytosis, protein concentration, opening pressure, and concentration of free anti-*Borrelia burgdorferi* antibody. Among the 31 neurologic Lyme disease CSF samples in the present study, we detected immune complexes in 21/31 (68%) cases. Isolated immune complexes, analyzed by ELISA were found to contain anti-*Borrelia burgdorferi* antibody. When free and complexed enriched CSF were examined for *Borrelia burgdorferi* antibody activity, patients with acute fulminant syndromes showed predominantly complexed antibody. This was particularly true for IgM. It appears that less than half of the CSF immune complexes detected in neuroborreliosis patients are *Borrelia burgdorferi* specific. One possibility that must be considered is that non-Borrelia specific CSF immune complexes may reflect an immune-mediated process, whose pathogenic importance remains to be proven, and which occurs in patients with the more chronic neurologic syndromes associated with Lyme disease. This possibility is supported by the reports in neurologic Lyme disease patients of IgM which cross reacts with *Borrelia burgdorferi* and human nerve tissue. Another study of Lyme radiculomyelitis identified *Borrelia burgdorferi*-specific and autoreactive (to peripheral and central nervous system autoantigens) CSF T cells. The demonstration of tissue binding cross reactive antibody might also help explain undetected free anti-*Borrelia burgdorferi* antibody. The detection of CSF immune complexes in the CNS compartment may be analogous to the accumulation of immune complexes that Hardin et al., Supra, described in the synovial compartment in Lyme arthritis. They were unable to detect compartmentalized *Borrelia burgdorferi* antigen.

In order to emphasis the significance of the immunopathogenic process we had chosen very rigorous thresholds that required positive values to exceed the mean plus 3SD. Perhaps less stringent thresholds might have more clinical utility. It should be remembered that immune reactivity to an infectious agent cannot be equated a priori with protective immunity as is dramatically illustrated in AIDS. However such reactivity in the form of a cellular or humoral response is indicative of exposure to the infectious agent.

Since current therapy is most efficacious in the earliest stages there is a need to establish the diagnosis at the onset. Specific signs such as ECM or bilateral facial palsy would strongly support the diagnosis of Lyme disease in the appropriate setting. The presence of other symptoms and signs of Lyme disease such as a flu-like illness, extreme fatigue, arthritis, peripheral and central neuropathies, meningitis, encephalitis, and cardiac conduction defects, engender a wide differential of diagnoses. Reliable laboratory tests are needed for diagnostic assistance.

In conclusion, these results demonstrate that apparent seronegativity in certain cases of Lyme disease may be explained by sequestration of antibody and that *Borrelia burgdorferi* antibody detection assays may have a broader utility when used in conjunction with immune complex isolation and dissociation techniques. Selective use of diagnostic assays such as antibody or antigen analysis of immune complex components may be helpful in establishing the diagnosis of Lyme disease in certain seronegative cases.

This invention may be embodied in other forms or carried out in other ways without departing from the spirit or essential characteristics thereof. The present disclosure is, therefore, to be considered as in all respects illustrative and not restrictive, the scope of the invention being indicated by the appended claims, and all changes which come within the meaning and range of equivalency are intended to be embraced therein.

What is claimed is:

1. A method for detecting the onset or presence of Lyme disease caused by *Borrelia burgdorferi* infection in a mammal, which comprises:
    A) collecting a biological sample from said mammal;
    B) isolating from said sample any immune complexes suspected of containing antibodies to *Borrelia burgdorferi*;
    C) dissociating any immune complexes isolated in step B) to release any of said antibodies to *Borrelia burgdorferi* present therein; and
    E) determining the presence of said antibodies through a specific binding reaction as indication of Lyme disease in said mammal.

2. The method of claim 1 wherein said biological sample is selected from the group consisting of synovial fluid, pericardial fluid, serum, cerebrospinal fluid and tissue.

3. The method of claim 2 wherein said biological sample is serum.

4. The method of claim 2 wherein said biological sample is cerebrospinal fluid.

5. The method of claim 1 wherein said immune complexes are isolated by with polyethylene glycol precipitation and said immune complexes are dissociated by treatment with a solution including sodium borate.

6. The method of claim 1 wherein said specific binding reaction is an immunochromatographic assay.

7. The method of claim 1 wherein said specific binding reaction is an enzyme immunoassay.

8. The method of claim 1 wherein said specific binding reaction is a radioimmunometric assay.

9. The method of claim 1 wherein isolating said immune complexes is performed by incubation with Raji cells.

10. The method of claim 1 wherein determining the presence of said antibodies of step D further comprises:
    i) immobilizing on a suitable solid support a specific binding partner directed to said antibodies to *Borrelia burgdorferi*;
    ii) incubating said support, the antibodies released in step C) and detectably labeled antibodies to *Borrelia burgdorferi*, wherein the labeled antibodies compete with the antibodies released for specific binding with the immobilized specific binding partner;
    iii) separating the material from step ii) which is bound to said support from the material not bound to said support; and
    iv) determining the presence of said labeled antibodies bound to said support, whereby the presence of said labeled antibodies is indicative of the presence of Lyme disease.

11. The method of claim 1 wherein determining the presence of said antibodies of step D further comprises:
    i) immobilizing on a suitable solid support antibodies to *Borrelia burgdorferi*;
    ii) incubating said support, the antibodies released in step C) and detectably labeled specific binding partner directed to said antibodies to *Borrelia burgdorferi* wherein the antibodies released compete with the antibodies immobilized on said support for binding with the labeled specific binding partner;

iii) separating the material from step ii) which is bound to said support from the material not bound to said support; and iv) determining the presence of the detectably labeled specific binding partner bound to said support, as an indication of the presence of Lyme disease.

12. The method of claim 1 wherein determining the presence of said antibodies of step D further comprises:

i) immobilizing on a suitable solid support a specific binding partner directed to said antibodies to *Borrelia burgdorferi;* ii) incubating said support, the antibodies released in step C) and detectably labeled anti-species antibodies which bind to the antibodies to *Borrelia burgdorferi* for a time and under conditions sufficient to form a complex bound to said support;

iii) separating the material from step ii) which is bound to said support from the material not bound to said support; and iv) determining the presence of said labeled anti-species antibodies bound to said support, whereby the presence of said labeled anti-species antibodies is indicative of the presence of Lyme disease.

13. The method of claim 10, 11, or 12 wherein the label is selected from the group consisting of an enzyme, and two or more enzymes.

14. The method of claim 13 wherein the label is selected from the group consisting of peroxidase, β-glucuronidase, β-D-glucosidase, β-D-galactosidase, urease, glucose oxidase plus peroxidase, galactose oxidase plus peroxidase, and alkaline phosphatase.

15. The method of claim 10, 11 or 12 wherein the label is a chemical which fluoresces when exposed to ultraviolet light.

16. The method of claim 15 wherein the chemical is selected from the group consisting of fluorescein, rhodamine, and auramine.

17. The method of claim 10, 11 or 12 wherein the label is a radioactive element.

18. The method of claim 17 wherein the radioactive element is selected from the group consisting of $^{14}C$, $^{125}I$, $^{131}I$, $^{35}S$, and $^{3}H$.

19. A method for detecting *Borrelia burgdorferi* infection of a mammal which comprises:

A) collecting a biological sample from said mammal;

B) isolating from said sample any immune complexes suspected of containing *Borrelia burgdorferi* antigen;

C) dissociating any immune complexes isolated in step B) to release any of said *Borrelia burgdorferi* antigen present therein; and E) determining the presence of said *Borrelia burgdorferi* antigen through a specific binding reaction as indication of *Borrelia burgdorferi* infection of said mammal.

* * * * *